US 10,772,684 B2

(12) United States Patent
Popovic et al.

(10) Patent No.: US 10,772,684 B2
(45) Date of Patent: Sep. 15, 2020

(54) SPATIAL VISUALIZATION OF INTERNAL MAMMARY ARTERY DURING MINIMALLY INVASIVE BYPASS SURGERY

(71) Applicant: KONINKLIJKE PHILIPS N.V., Eindhoven (NL)

(72) Inventors: Aleksandra Popovic, Bostom, MA (US); Haytham Elhawary, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 447 days.

(21) Appl. No.: 15/116,929

(22) PCT Filed: Jan. 28, 2015

(86) PCT No.: PCT/IB2015/050631
§ 371 (c)(1),
(2) Date: Aug. 5, 2016

(87) PCT Pub. No.: WO2015/121764
PCT Pub. Date: Aug. 20, 2015

(65) Prior Publication Data
US 2017/0172663 A1  Jun. 22, 2017

Related U.S. Application Data

(60) Provisional application No. 61/938,540, filed on Feb. 11, 2014.

(51) Int. Cl.
*A61B 34/10* (2016.01)
*A61B 1/00* (2006.01)
(Continued)

(52) U.S. Cl.
CPC .......... *A61B 34/10* (2016.02); *A61B 1/00147* (2013.01); *A61B 34/30* (2016.02);
(Continued)

(58) Field of Classification Search
CPC ....... A61B 34/10; A61B 34/30; A61B 90/361; A61B 90/37; A61B 1/00147; A61B 1/04; G06T 7/30; H04N 5/23293; H04N 5/265
(Continued)

(56) References Cited

U.S. PATENT DOCUMENTS

| | | | |
|---|---|---|---|
| 6,346,940 B1* | 2/2002 | Fukunaga | G06T 15/20 345/420 |
| 6,591,130 B2* | 7/2003 | Shahidi | A61B 5/06 600/117 |

(Continued)

FOREIGN PATENT DOCUMENTS

| CN | 201840505 U | 5/2011 |
|---|---|---|
| CN | 102784003 A | 11/2012 |

(Continued)

OTHER PUBLICATIONS

Cha, Kwang Soo Et L "Feasibility and Safety of Concomitant Left Internal Mammary Arteriography at the Setting of the Right Transradial Coronary Angiography", Catheterization and Cardiovascular Interventions, vol. 58, 2002, pp. 188-195.

*Primary Examiner* — Timothy J Neal
*Assistant Examiner* — William B Chou

(57) ABSTRACT

A system for visualizing an anatomical target includes an imaging device having a field of view for imaging a portion of a region to be imaged. A three-dimensional model is generated from pre-operative or intra-operative images and includes images of an internal volume in the region to be imaged not visible in the images from the imaging device. An image processing module is configured to receive images from the imaging device such that field of view images of the imaging device are stitched together to generate a composite image of the region to be imaged. The composite image is registered to real-time images and the three-dimensional model. An internal view module is configured (Continued)

to generate for display an internal view of the internal volume at one or more positions along the composite image.

21 Claims, 3 Drawing Sheets

(51) Int. Cl.
    *A61B 90/00*     (2016.01)
    *G06T 7/30*     (2017.01)
    *A61B 34/30*     (2016.01)
    *H04N 5/232*     (2006.01)
    *H04N 5/265*     (2006.01)
    *G06T 17/00*     (2006.01)

(52) U.S. Cl.
    CPC ............ *A61B 90/361* (2016.02); *A61B 90/37* (2016.02); *G06T 7/30* (2017.01); *H04N 5/23293* (2013.01); *H04N 5/265* (2013.01); *A61B 2034/101* (2016.02); *A61B 2034/302* (2016.02); *A61B 2090/365* (2016.02); *G06T 17/00* (2013.01); *G06T 2207/10068* (2013.01); *G06T 2207/10072* (2013.01); *G06T 2207/30101* (2013.01)

(58) Field of Classification Search
    USPC ........ 600/109, 117, 118, 139, 145, 153, 160
    See application file for complete search history.

(56) References Cited

U.S. PATENT DOCUMENTS

| | | | |
|---|---|---|---|
| 7,343,195 B2 | 3/2008 | Strommer et al. | |
| 8,805,003 B2 | 8/2014 | Villain et al. | |
| 8,831,303 B2 | 9/2014 | Villain et al. | |
| 2002/0049375 A1 | 4/2002 | Strommer | |
| 2003/0018235 A1* | 1/2003 | Chen | A61B 1/00009 600/109 |
| 2005/0015005 A1* | 1/2005 | Kockro | A61B 90/36 600/427 |
| 2006/0020213 A1* | 1/2006 | Whitman | A61B 1/05 600/478 |
| 2008/0247621 A1 | 10/2008 | Zarkh et al. | |
| 2010/0149183 A1* | 6/2010 | Loewke | G06K 9/00134 345/424 |
| 2011/0190774 A1* | 8/2011 | Nikolchev | A61B 17/56 606/90 |
| 2011/0282151 A1 | 11/2011 | Trovato | |
| 2012/0287238 A1* | 11/2012 | Onishi | A61B 1/0005 348/45 |
| 2013/0303893 A1* | 11/2013 | Duindam | A61B 5/066 600/424 |
| 2014/0110007 A1 | 6/2014 | Manzke et al. | |
| 2014/0343416 A1* | 11/2014 | Panescu | A61B 34/30 600/431 |
| 2015/0073265 A1 | 3/2015 | Popovic et al. | |
| 2015/0112126 A1 | 4/2015 | Popovic et al. | |
| 2016/0302869 A1* | 10/2016 | Chopra | G16H 50/50 |
| 2017/0007350 A1 | 1/2017 | Popovic et al. | |
| 2017/0172663 A1* | 6/2017 | Popovic | A61B 34/10 |
| 2017/0189118 A1* | 7/2017 | Chopra | A61B 34/30 |

FOREIGN PATENT DOCUMENTS

| | | |
|---|---|---|
| JP | 2006198032 A | 8/2006 |
| WO | 2012035492 A1 | 3/2012 |
| WO | 2013072818 A1 | 5/2013 |
| WO | 2014001980 A1 | 1/2014 |

* cited by examiner

SPATIAL VISUALIZATION OF INTERNAL MAMMARY ARTERY DURING MINIMALLY INVASIVE BYPASS SURGERY

CROSS-REFERENCE TO PRIOR APPLICATIONS

This application is the U.S. National Phase application under 35 U.S.C. § 371 of International Application No. PCT/IB2015/050631, filed on Jan. 28, 2015, which claims the benefit of U.S. Provisional Patent Application No. 61/938,540, filed on Feb. 11, 2014. These applications are hereby incorporated by reference herein.

BACKGROUND

Technical Field

This disclosure relates to medical instruments and methods and, more particularly, to systems and methods for improved visualization of internal anatomy in medical applications.

Description of the Related Art

Coronary artery bypass grafting (CABG) is a surgical procedure for revascularization of obstructed coronary arteries. In conventional surgery, the patient's sternum is opened, and the heart is fully exposed. However, minimally invasive (MI) bypass surgery is performed through small ports between the ribs. An important part of a CABG procedure is the removal of a vessel from the patient's body, which is then used to bypass one or more atherosclerotic narrowings in the coronary arteries. The vessel most commonly removed and used is an Internal Mammary Artery (IMA), which may include a Left IMA (LIMA) or Right IMA (RIMA), which are located in the thoracic cavity.

During MI cardiac bypass surgery direct access to these vessels is not available, and they are removed using long instruments inserted into ports through intercostal muscles in spaces between the ribs. During MI surgery, a surgical assistant can hold the endoscope, or it can be held using robotic guidance. In the case of robotic guidance, visual servoing can be used to move the robot to a specific location. Visual servoing consists of selecting a point on the endoscope image, with the robot moving in such a way that the point becomes located in the center of the image.

IMA takedown is usually the most time consuming part of the CABG procedure. IMA takedown usually takes between 45-60 minutes, and the success of a bypass procedure usually depends on the quality of the harvested vessel.

The main challenges during this stage of procedure include the following. Endoscope images are the only visualization method for this procedure, but the endoscope provides only a limited view of a small segment of a blood vessel. For MI, a surgeon works with elongated instruments inserted between the ribs reaching below the sternum area. This makes it difficult since the artery being harvested needs to be carefully isolated from surrounding tissue and side branches have to be cauterized.

A length of, e.g., the LIMA artery, has to be sufficient to reach the bypass location on the coronary artery. It is very difficult to estimate the length of the harvested vessel artery during MI procedures (as opposed to open surgery, where the length can be estimated since all areas are visible and accessible). As the LIMA is removed from the middle and inferior part of the chest, it tends to be more embedded in the tissue, slowing down isolation and making visualization of the artery and side branches even more challenging.

The combination of technical difficulties for artery isolation and the unknown length needed for bypass contributes to an extended procedure time, as the surgeon either isolates a much longer arterial segment than needed in the more challenging distal area, or isolates too short a segment, which requires returning later for continued isolation of the artery.

The IMA is usually embedded into the tissue at the chest wall. An endoscope view alone may not be sufficient to expose all of the IMA branches. A failure to close (e.g., cauterize or clip) the side branches of the IMA when removing it from the chest wall will cause leakage on the bypassed artery that may cause further injury.

SUMMARY

In accordance with the present principles, a system for visualizing an anatomical target includes an imaging device having a field of view for imaging a portion of a region to be imaged. A three-dimensional model is generated from pre- or intra operative images and includes images of an internal volume in the region to be imaged not visible in the images from the imaging device. An image processing module is configured to receive images from the imaging device such that field of view images of the imaging device are stitched together to generate a composite image of the region to be imaged. The composite image is registered to real-time images and the three-dimensional model. An internal view module is configured to generate for display an internal view of the internal volume at one or more positions along the composite image.

Another system for visualizing an anatomical target includes a processor and memory coupled to the processor. The memory includes a three-dimensional model generated from pre- or intra-operative images and including images of an internal volume in the anatomical target, and an image processing module configured to receive real-time images and stitch together portions of the real-time images to generate a composite image of the anatomical target, the image processing module being configured to register the composite image to the real-time images and the three-dimensional model. An internal view module is configured to generate for display an internal view of the internal volume inside the anatomical target at one or more positions along the composite image.

A method for visualizing an anatomical target includes imaging portions of an anatomical target using a field of view of a scope; forming a composite image of the anatomical target using the portions; registering points of interest in the composite image with real-time images and a three-dimensional model of an internal volume of the anatomical target; and concurrently displaying the real-time images, the composite image and images of the internal volume at one or more selected positions along the composite image.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
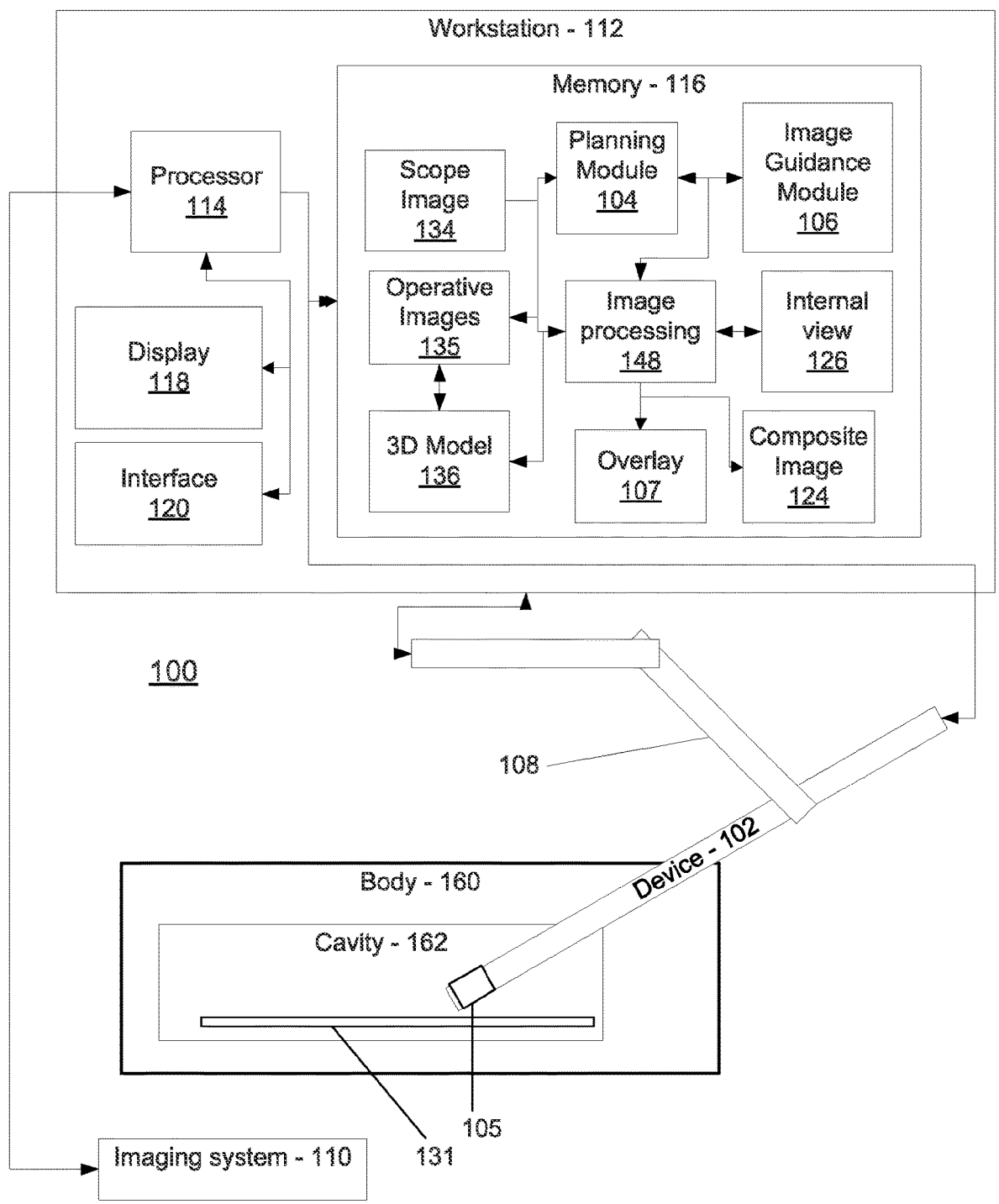
FIG. 1 is a block/flow diagram showing a system for visualizing an anatomical target in accordance with one embodiment.

In accordance with the present principles, a blood vessel isolation planning and execution system is provided to solve the problems of vessel isolation as described above. The present principles provide a significantly enlarged field-of-view showing most of the blood vessel (e.g., the LIMA) as opposed to only a small segment and provide additional information about the blood vessel. This additional information includes, e.g., the length of the blood vessel being isolated for harvesting, the progress of the blood vessel isolation with respect to a desired bypass length and the location of side branches that need to be cauterized.

In addition to showing arteries from pre-operative three-dimensional (3D) images overlaid and fused with an endoscope image, which tends to be a planar relationship, the arteries are projected onto the endoscope image indicating their depth in the chest wall at which the IMA and branches are embedded. Without this depth knowledge, it would otherwise be difficult for a surgeon to decide the tissue-depth at which takedown will take place or decide how much facia to remove from the chest wall. Without such depth information, this could lead to branches not being properly cauterized and take excessive time to remove the IMA from the chest wall. A left internal mammary artery (LIMA) runs under the ribs with numerous branches. This vessel may be removed from the chest wall to be used in a cardiac bypass.

In accordance with particularly useful embodiments, systems and methods are provided to visualize spatial relationships between the internal mammary artery (or other vessels) and its side-branches during artery take-down for minimally invasive coronary bypass surgery. Systems include a virtual visualization of a cross section of a blood vessel (e.g., an artery) from pre-operative 3D images and a method for robotic guided endoscope manipulation to inspect the artery prior to takedown. The present principles avoid the need to perform preoperative diagnostic catheterization of the IMA, which may be risky and may cause injury to the vessel.

It should be understood that the present invention will be described in terms of medical instruments for use with and for a coronary bypass procedure; however, the teachings of the present invention are much broader and are applicable to any instrument or procedure where enhanced visualization of a target anatomy is needed or desired. In some embodiments, the present principles are employed in tracking, manipulating or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for minimally invasive surgery is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store a planning module 104 and an image guidance module 106 employed to work in conjunction with a medical device 102. The medical device 102 may include an imaging device 105 (e.g., camera, fiber optics with lens, etc.) that may be deployed with one or more of a catheter, a guidewire, a probe, an endoscope, a flexible endoscope, a robot, an electrode, a filter device, a balloon device, or other medical component, etc. The device 102 may be inserted into a body 160 of a patient. In one embodiment, a procedure to be performed includes minimally invasive coronary surgery, and the device 102 is inserted into a thoracic cavity 162 of the body 160 to observe and isolate an anatomical target 131, such as a blood vessel (e.g., an IMA).

The planning module 104 includes the following elements and features. During, e.g., a vessel take-down for a coronary bypass procedure, the planning module 104 plans for the control of visualization of a target vessel to be harvested, e.g., the IMA, while permitting a surgeon to manipulate other instruments. The planning module 104 stores a plan for manipulating a robot 108 or providing guidance to an operator during a manual procedure.

An image processing module 148 controls image stitching along the IMA to provide a comprehensive field of view, and further provides image registration permitting overlaying of preoperative (or intra-operative) images on, e.g., an endoscope video using methods known in art. The planning module 104 provides for the selection of target points of interest, which can be referred to or indexed for use with the image guidance module 106. The planning module 104 also provides for computation of blood vessel or other anatomical feature lengths (e.g., using the stitched/composite image).

The image processing module 148 may be employed to register and overlay operative images 135, such as preoperative or intraoperative images taken using an imaging device 110. The imaging device 110 may be employed contemporaneously or at another time and location to collect the images. The operative images 135 may include three dimensional preoperative computed tomography (CT) images or magnetic resonance images (MRI), etc. or intra-operative X-rays or ultrasound. Other imaging modalities are also contemplated. The operative images 135 are employed to build a three-dimensional model 136 including virtual internal cross-section or internal view images along the anatomical target 131.

The image guidance module 106 provides image-based control of the device 102, e.g., an endoscope, preferably by controlling a robotic system 108, which supports the device 102. An overlay 107 may be generated using the image processing module 148 and the planning module 104. The overlay 107 may include a current live endoscope image 134 visualized on a composite image 124. The composite image 124 is the stitched together view of a plurality of fields of view of images taken by the device 102. The image guidance module 106 provides quantification for progress which can compare a length of isolated vessel to a desired length to determine when sufficient progress has been achieved.

The image guidance module 106 guides the robot system 108 along the length of the target anatomy 131. In one embodiment, the device 102 is guided using the points of interest assigned during a planning stage and stored in a plan in the planning module 104.

Workstation 112 includes a display 118 for viewing internal images of a subject (patient) or volume and may include images with an overlay or other rendering generated over images collected from the device 102. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

The operative images 135 of the anatomical target 131 may include 3D images of an IMA. During a diagnostic or preoperative scan of the patient anatomy, a 3D angiographic scan may be acquired. The scan can be extended if needed to visualize the IMA as well. (See e.g. FIG. 2, image 202). From the scan, a 3D model 136 of IMA can be reconstructed.

For example, from the scanned image, a segmentation method, which may be a method known in the art, can be employed to generate a 3D surface of the IMA, with all its branches. Next, generation of virtual angiography IMA images is obtained from a camera viewpoint inside the vessel (see, e.g., FIG. 2, image 204). A first step for the generation of virtual images may include a detection of the centerline of the vessel structure. The centerline can be computed using skeletonization, which finds a line in the center of vessels while minimizing distance from the line to the vessel walls. This method is well-suited to the applications in accordance with the present principles since one purpose is to show spatial branching of the vessel.

Figure 2:
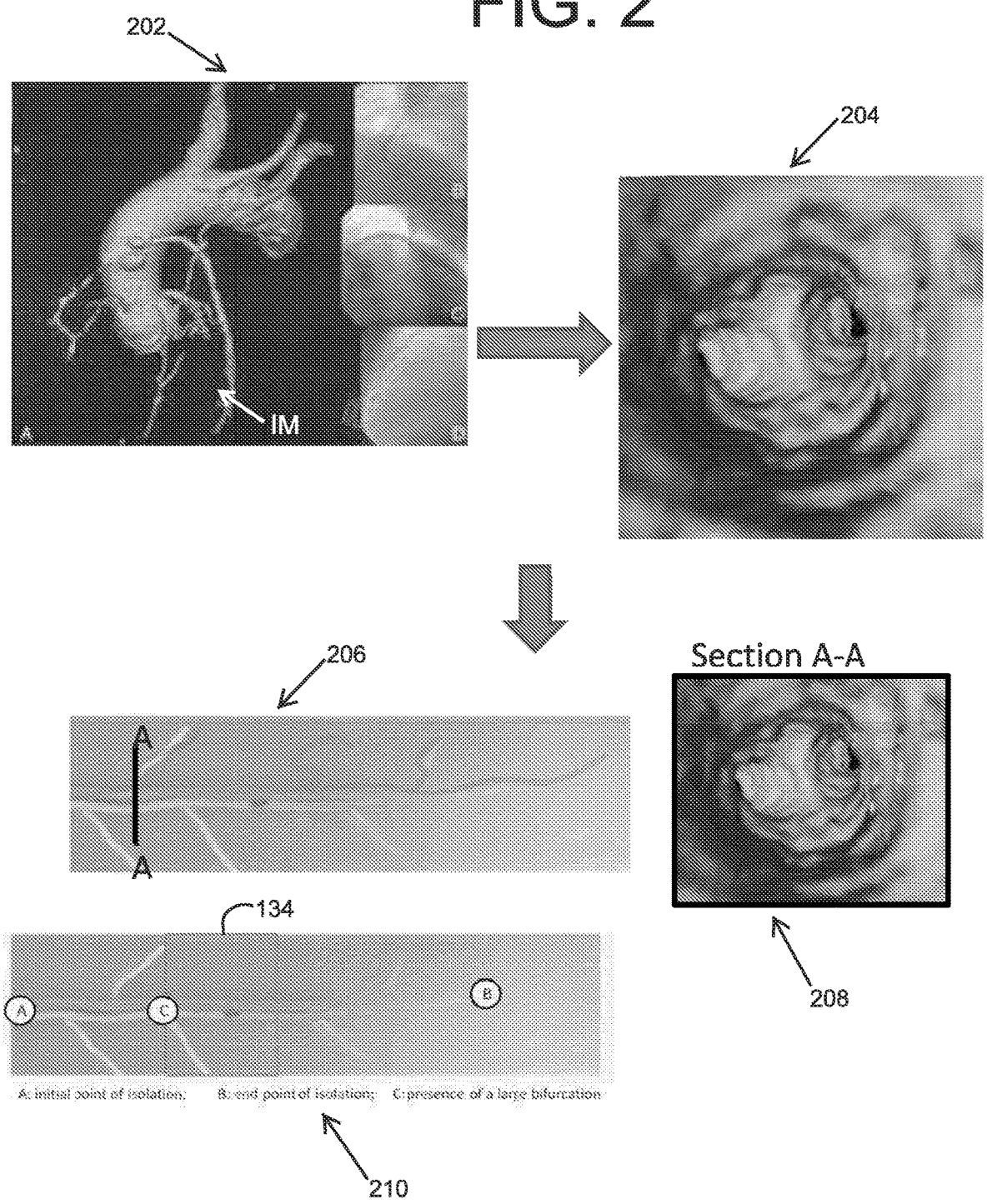
FIG. 2 is a diagram showing images employed in rendering a composite view with internal cross-sectional images of a blood vessel in accordance with the present principles.

Then, panoramic stitching of IMA images and registration with the 3D model is performed (see, e.g., FIG. 2, image 206). The method to perform the registration and stitching may include image stitching for a wide field of view image. With the endoscope 102 in place and located towards a beginning (end) of the LIMA vessel, a surgeon can start the acquisition of a wide field of view. To do so, the surgeon or a robot 108 moves the endoscope 102 using uncalibrated robotic visual servoing or other technique along the visible portion of the LIMA. In this way, the surgeon selects points along the LIMA, and the endoscope 102 moves accordingly. The surgeon can also use a surgical instrument as a guide, as the instrument moves, and then the endoscope can follow the tool tip. This step is analogous to clinical practice, where the endoscope is moved either by an assistant or surgeon to observe the entire length of artery.

To stitch the images collected by the moving endoscope 102, known methods used to perform stitching of the images may be modified. The images may employ matching algorithms (148) or other image processing techniques. One modification relates to the endoscope type. In this embodiment, the endoscope 102 can be either or both of oblique and forward viewing. A second modification relates to the motion of the endoscope 102. The motion of endoscope may be pre-programmed and gated by the image processing module 148. In this embodiment, the motion is generated and gated by the surgeon's commands. Another feature may include the use of a flexible endoscope.

Although the motion is defined by the user, the verification of images captured used for stitching can be performed by optimizing captured images based on the amount of overlap and residual error in red, green, blue (RGB) values of overlapped pixels. Images are aligned to form the composite image 124. The composite image 124 includes an entire length of the blood vessel (e.g., IMA). A total length of the blood vessel may be computed from the image (using a scale or reference) or may be computed based upon a distance traveled by the endoscope or other tool in the images. The final result is the composite image 124, which includes a series of images (field of view images) along the length of IMA 131, which have been stitched together from individual images acquired by the endoscope over a time period.

The composite image 124 has points of interest selected and indicated in the image. Once the composite image 124 of a relevant part of the IMA 131 has been generated, several anatomical points of interest on the composite image can be selected to plan for vessel isolation. These points can be stored (by overlaying them on the image), and then referred to during the procedure. Alternately, as the points are selected, the robot 108 (endoscope holder) moves the endoscope 102 to that location, and the joint positions of the robot 108 are stored, so they can be referred to during the image guided isolation procedure.

The selection of points on the anatomical points of interest may include, e.g., an initial point of isolation, an end point of isolation and a large bifurcation or other anatomical feature or point. In addition (or alternatively) to the selection of points on the composite image 124, the composite image 124 can be used to register the endoscope image (134) and preoperative or intraoperative 3D imaging (3D model 136). The overlay 107 may include real-time images (134) and the composite image 124 using image processing 148. A comparison of the composite image 124 with the IMA 131 can indicate the location of bifurcations that are not directly visible on the endoscope images, as they could be located underneath fascia and other tissue.

The 3D model 136 may also be registered with the overlay 107 (including real-time images 134 and composite image 124) to reveal internal structures within the anatomical target 131 (from the 3D model 136). This may include the generation of a cross-sectional image at a position of the endoscope 102, at a point selected by an operator, selected by robot position, etc.

After a first run (tracing a path of the target 131) with the robot 108 along the blood vessel (e.g., artery), the robot 108 remembers where every position of the artery is (from encoders) and then can retrace the path later visualizing the endoscope image (live) and an internal view (e.g., a cross section(s) from pre- or intra-operative 3D images). An internal view module 126 may be part of the planning module 104, be part of the image processing module 148 or exist as a separate module. The internal view module 126 generates internal view images from structure images in the operative images 135/model 136 and in particular, e.g., cross-sectional views, of blood vessels along the composite image 124.

Referring to FIG. 2, a diagram illustratively shows images employed at different stages in providing a composite image with available cross-sectional views of a vessel in accordance with the present principles. Image 202 shows a 3D angiographic image, which includes the IMA vessel. The acquisition of the 3D image 202 of the IMA may be taken during diagnostic or preoperative scans of the patient anatomy. The 3D angiographic scan may need to be extended from conventional procedures to visualize the entire IMA.

A segmentation of the IMA vessel is then performed to provide data features for the main vessel and branches. Reconstruction of a segmented 3D model of IMA is provided from the scanned image. Any suitable segmentation method may be performed to generate a 3D surface of the IMA, with all its branches.

Virtual angiography IMA images are generated from a camera viewpoint inside the vessel. An image 204 shows a virtual 3D image from a camera viewpoint inside of the vessel showing branched portions. The generation of virtual images includes a detection of the centerline of the vessel structure. The centerline can be computed using skeletonization, which finds a line in the center of vessels while minimizing distance from the line to the vessel walls. These images show spatial branching of the vessel.

A composite endoscope image 206 is stitched together from multiple endoscope images. A panoramic stitching of IMA images puts together a plurality of endoscopic images to provide a complete view of the IMA or other target. The panoramic view is registered with the 3D model. In this way, an internal image is available for any point along the vessel. The composite endoscope image 206 is registered with the 3D renderings (3D model with the internal camera images). The image 206 shows the vessel with a cross section line (e.g., at section line A-A) so a surgeon can see spatial disposition of branches with respect to the main IMA vessel as shown in image 208. Image 208 shows the internal camera view at section line A-A. A viewing position (e.g., section A-A) may be moved along the vessel in image 206, and image 208 would be updated accordingly with the associated virtual image for that position.

In one embodiment, selection of a cross section of IMA in the endoscope images and visualization of virtual images related to that cross section is provided. The selection of a position on the IMA may be performed using the interface 120 (FIG. 1) and the display 118 (FIG. 1). The user selects a position on the IMA, and the system displays the virtual image from inside the vessel (e.g., cross-section).

In another embodiment, automatic visualization may be employed and controlled by the positioning of the endoscope or other device. For example, the vessel cross section may be rendered for a position corresponding to a center of the endoscope image. The cross-section image (virtual image) can be automatically selected and the cross section 3D view can be generated and visualized by the surgeon.

In another embodiment, robotic guidance of the endoscope along the IMA may be provided with visualization of the corresponding cross section. The vessel cross section at the center of the endoscope image can be automatically selected, and the cross section 3D view can be generated and visualized by the surgeon. The robotically manipulated endoscope may be positioned at the proximal end of the IMA, close to the aorta. Based on the image stitching and the known values of the robot encoders associated with every position in the panoramic image 206, the robotic system can move the endoscope to follow the IMA over its length at a velocity defined by the user. As the endoscope moves, both the image of the endoscope 206 as well as the virtual image 208 reconstruction of the IMA may be concurrently shown.

Referring to again to FIG. 1 with continued reference to FIG. 2, the image guidance module 106 is employed to guide the endoscope 102. The surgeon moves the endoscope back to a proximal position (point "A" in image 210), e.g., close to the aorta, and starts performing the isolation of the artery from the surrounding tissue to detach the artery (IMA) from the chest wall. The surgeon can automatically locate the endoscope at that location by using visual servoing and/or referring to previously selected points, e.g., point "C", selected during planning and showing a large bifurcation. As the surgeon progresses along the artery, both a current endoscope view (scope image 134 in image 210) which may be overlaid on the previously computed composite image 124 or displayed concurrently to the surgeon. In addition, an overlay of a section line (A-A in image 206) or other point of interest may be provided to further display an interior view of the artery being viewed. The interior camera view 208 is provided from the preoperative images.

The "picture in a picture" view permits the surgeon to observe a much wider field of view than what is currently available and to view interior portions of the blood vessel to reveal any branching, damaged tissue or other features of interest not available in the endoscope view. In addition, as the motion of the endoscope is known from robot encoders combined with the registration information, a scale can be retrieved, showing the length of the portion of artery that is already isolated or a planned endpoint (point "B") of the vessel to be isolated.

While the present principles have been described for a CABG procedure using an IMA, the devices (robotic endoscope moving along the target artery) and visualization methods described herein may be applied in other areas of the body, and for other procedures. Particularly useful applications of are employed in minimally invasive bypass surgery, although the present principles may be employed for any procedure that employs vessel isolation.

Figure 3:
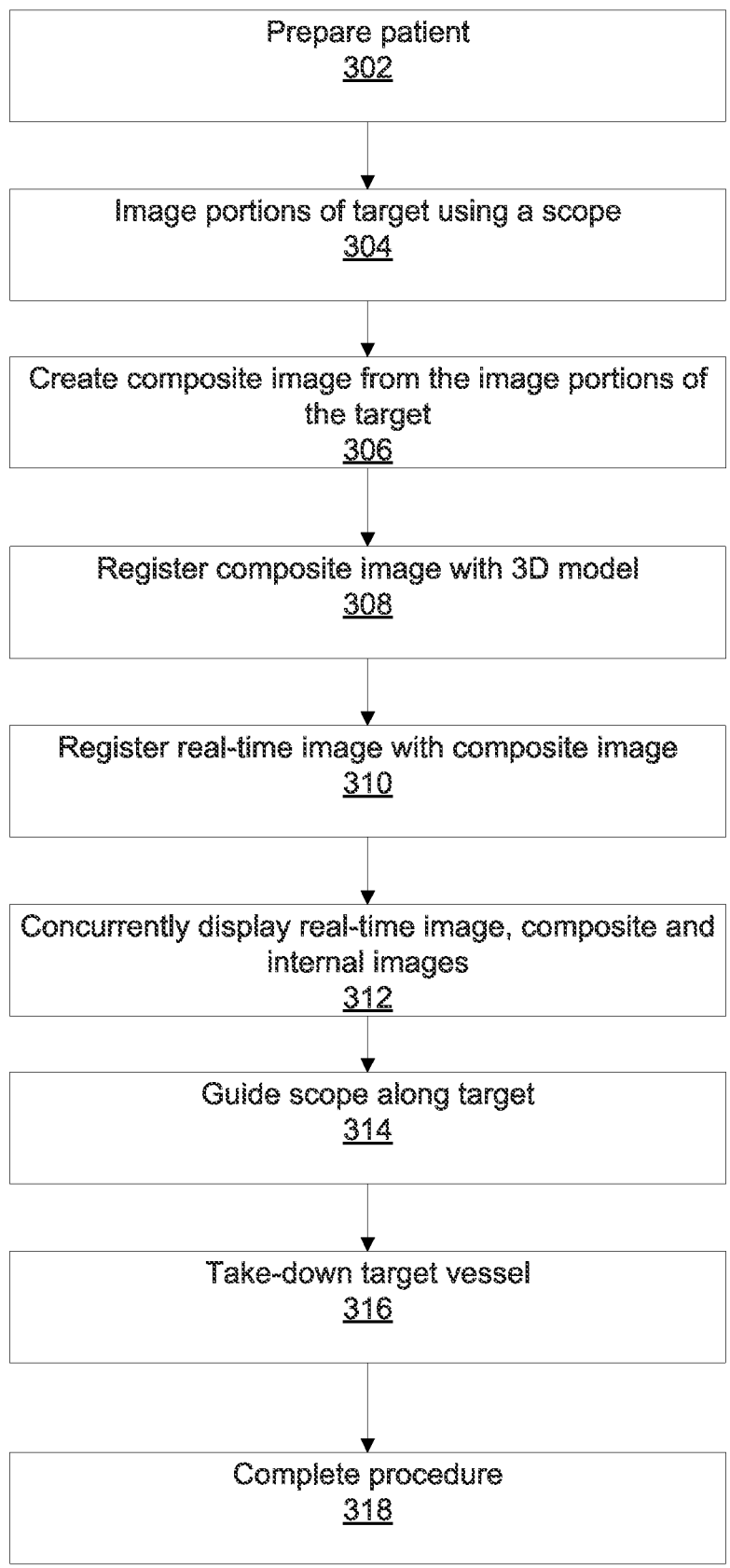
FIG. 3 is a flow diagram showing a method for visualizing an anatomical target in accordance with illustrative embodiments.

Referring to FIG. 3, a method for visualizing an anatomical target is illustratively shown in accordance with the present principles. In block 302, in one embodiment, a patient is prepared for an interventional procedure. This includes preoperative imaging to create a three-dimensional (3D) model of an anatomical target. The three-dimensional model may be generated using a preoperative three-dimensional angiographic scan. Other scanning technologies may also be employed. A detailed plan may be generated using the 3D images/model including designated points or interest. An incision and/or port provide access to an interior of a patient in which instruments are installed.

In block 304, portions of an anatomical target are imaged using a field of view of a scope (e.g., an endoscope). The field of view of each image may be less than the entire region or anatomical target. In block 306, a composite image of the anatomical target is formed using the portions of the images in a plurality of the fields of view of the scope. This may include stitching the portions together to make the composite image. In block 308, points of interest in the composite image are registered with a three-dimensional model of an internal volume of the anatomical target. In block 310, the composite image is registered with a real-time scope image.

In block 312, the real-time image, the composite image and images of the internal volume are provided for concurrent display at one or more selected positions along the anatomical target and/or the composite image. The selected points of interest may include any number of points and provide a technician/surgeon internal details of the blood vessel (e.g., its depth) or other target along the entire length of the target. At each point of interest as provided on the composite image (e.g., used as a map) and/or target, a cross-sectional view or internal camera view of the interior of the blood vessel can be displayed for the technician/surgeon that corresponds to the selected point or points of interest.

In block 314, the scope is guided (e.g., manually or with a robot) along the anatomical target and the one or more selected positions along the composite image are employed to trigger viewing of the corresponding internal images. The anatomical target may include a blood vessel to be isolated, and the images of the internal volume preferably reveal branches to be cauterized in an internal mammary artery (IMA) for use in bypass surgery. As the scope is guided along the anatomical target (and viewed by the scope), the corresponding internal images may also be displayed to detect branching or other features. In block 316, a blood vessel takedown is performed using the composite image and internal views in accordance with the present principles to ensure that all branches are cauterized and a sufficient length of the vessel is harvested. In block 318, the procedure is completed.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for spatial visualization of internal mammary artery during minimally invasive bypass surgery (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for visualizing an anatomical target, comprising:

an imaging device insertable into a body including the anatomical target, the imaging device having a field of view for imaging at least a portion of a region to be imaged and providing real-time images;

a three-dimensional model comprising virtual internal cross-section images, generated from pre-operative or intra-operative images and including images of an internal volume in the region to be imaged not visible in the real-time images from the imaging device;

an image processing module configured to receive the real-time images from the imaging device and stitch together portions of the real-time images from the imaging device to generate a composite image of the region to be imaged, the composite image being registered to the real-time images received from the imaging device and the three-dimensional model; and an internal view module configured to generate for display an internal view of the internal volume at one or more positions along the composite image.

2. The system as recited in claim 1, further comprising a robot configured to guide the imaging device in accordance with an image guidance module.

3. The system as recited in claim 2, wherein the robot is configured to traverse a path and the internal view module is configured to generate the internal view for display as the path is traversed.

4. The system as recited in claim 1, wherein the region to be imaged includes a blood vessel to be isolated and the internal view reveals branches to be cauterized.

5. The system as recited in claim 1, wherein the internal view module is configured to generate a cross section of a blood vessel along the composite image.

6. The system as recited in claim 5, wherein the blood vessel includes an internal mammary artery (IMA) for use in bypass surgery.

7. The system as recited in claim 1, further comprising a display device configured to concurrently display two or more of the composite image, the real-time images or images of the internal view at one or more selected positions along the composite image.

8. The system as recited in claim 1, wherein the three-dimensional model is generated using a preoperative three-dimensional angiographic scan.

9. A system for visualizing an anatomical target, comprising:

a processor;

memory coupled to the processor, the memory including:
- a three-dimensional model comprising virtual internal cross-section images, the three-dimensional model being generated from pre-operative or intra-operative images and including images of an internal volume in the anatomical target;
- an image processing module configured to receive real-time images from an imaging device insertable into a body including the anatomical target, and stitch together portions of the real-time images to generate a composite image of the anatomical target, the image processing module being configured to register the composite image to the real-time images and the three-dimensional model; and
- an internal view module configured to generate for display an internal view of the internal volume inside the anatomical target at one or more positions along the composite image.

10. The system as recited in claim 9, further comprising a robot configured to guide a scope in accordance with an image guidance module for collecting the real-time images.

11. The system as recited in claim 10, wherein the robot is configured to traverse a path and the internal view module is configured to generate the internal view for display as the path is traversed.

12. The system as recited in claim 9, wherein a region to be imaged includes a blood vessel to be isolated and the internal view reveals branches to be cauterized.

13. The system as recited in claim 9, wherein the internal view module is configured to generate a cross section of a blood vessel along the composite image.

14. The system as recited in claim 13, wherein the blood vessel includes an internal mammary artery (IMA) for use in bypass surgery.

15. The system as recited in claim 9, further comprising a display device configured to concurrently display two or more of the composite image, the real-time images or images of the internal view at one or more selected positions along the composite image.

16. The system as recited in claim 9, wherein the three-dimensional model is generated using a preoperative three-dimensional angiographic scan.

17. A method for visualizing an anatomical target, comprising acts of:
- imaging portions of the anatomical target using a field of view of a scope to obtain real-time images;
- generating a three-dimensional model comprising virtual internal cross-section images from pre-operative or intra-operative images and including images of an internal volume in a region to be imaged not visible in the real-time images from the scope;
- forming a composite image of the anatomical target using portions of the real-time images;
- registering points of interest in the composite image with the real-time images and the three-dimensional model of the internal volume; and
- concurrently displaying the real-time images, the composite image and images of the internal volume at one or more selected positions along the composite image.

18. The method as recited in claim 17, further comprising an act of guiding a robot along the anatomical target and displaying the images of the internal volume for the one or more selected positions along the composite image.

19. The method as recited in claim 17, wherein the anatomical target includes a blood vessel to be isolated and the images of the internal volume reveal branches to be cauterized in an internal mammary artery (IMA) for use in bypass surgery.

20. The method as recited in claim 17, wherein the three-dimensional model is generated using a preoperative three-dimensional angiographic scan.

21. A system for visualizing an anatomical target, comprising:
- an imager having a field of view for imaging at least a portion of a region to be imaged;
- a memory configured to store a three-dimensional model comprising virtual internal cross-section images, generated from pre-operative or intra-operative images and including images of an internal volume in the region to be imaged not visible in the images from the imager; and
- a processor operably coupled to the imager and the memory, the processor being configured to:
  - receive images from the imager and stitch together the images from the imager to generate a composite image of the region to be imaged;
  - register the composite image with real-time images and the three-dimensional model; and
  - generate for display an internal view of the internal volume at one or more positions along the composite image.

* * * * *